(12) United States Patent
Yun et al.

(10) Patent No.: US 11,981,632 B2
(45) Date of Patent: May 14, 2024

(54) PROCESS FOR PRODUCING HYDROGEN, CARBON, AND ETHYLENE FROM METHANE-CONTAINING FEEDSTOCK

(71) Applicant: SK Innovation Co., Ltd., Seoul (KR)

(72) Inventors: Dong Min Yun, Daejeon (KR); Hee Soo Kim, Daejeon (KR); Ji Hoon Lee, Daejeon (KR); Jung Geun Jang, Daejeon (KR); Dae Hyun Choo, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 17/976,045

(22) Filed: Oct. 28, 2022

(65) Prior Publication Data
US 2023/0133746 A1 May 4, 2023

(30) Foreign Application Priority Data
Oct. 29, 2021 (KR) .................. 10-2021-0146261

(51) Int. Cl.
*C07C 5/09* (2006.01)
*B01J 21/04* (2006.01)
(Continued)

(52) U.S. Cl.
CPC .................. *C07C 5/09* (2013.01); *B01J 21/04* (2013.01); *B01J 23/745* (2013.01); *C01B 3/26* (2013.01);
(Continued)

(58) Field of Classification Search
CPC .... C07C 5/09; C07C 2/78; C07C 2/80; C07C 2/84; C07C 7/09; C07C 2521/04;
(Continued)

(56) References Cited

U.S. PATENT DOCUMENTS

| 7,199,273 B2 * | 4/2007 | Molinier | ................. B01J 23/62 |
| | | | 585/258 |
| 2002/0007594 A1 * | 1/2002 | Muradov | ............. B01J 19/2475 |
| | | | 48/78 |
| 2016/0362351 A1 * | 12/2016 | Nagaki | ................. B01J 23/745 |

FOREIGN PATENT DOCUMENTS

KR 1020180113448 A 10/2018

OTHER PUBLICATIONS

Sanchez-Bastardo et al. ("Methane Pyrolysis for CO2-Free H2 Production: A Green Process to Overcome Renewable Energies Unsteadiness." Chemie Ingenieur Technik 92.10 (2020): 1596-1609) (Year: 2020).*

(Continued)

*Primary Examiner* — In Suk C Bullock
*Assistant Examiner* — Jason Y Chong
(74) *Attorney, Agent, or Firm* — The Webb Law Firm

(57) ABSTRACT

Disclosed is a method for producing hydrogen, carbon, and ethylene from a methane-containing feedstock even without recycling of unreacted methane by providing a single process or system in which a methane-containing feedstock is subjected to two methane conversion steps. The method includes a first conversion step of producing hydrogen and carbonaceous materials and a second conversion step of producing acetylene from unreacted methane and hydrogen discharged from the first conversion step while maintaining a good methane conversion and suppressing coke formation, followed by separating and recovering ethylene and hydrogen produced through selective hydrogenation of acetylene.

14 Claims, 5 Drawing Sheets

(51) Int. Cl.
| | |
|---|---|
| *B01J 23/745* | (2006.01) |
| *C01B 3/26* | (2006.01) |
| *C01B 32/05* | (2017.01) |
| *C01B 32/162* | (2017.01) |
| *C01B 32/205* | (2017.01) |
| *C07C 2/76* | (2006.01) |
| *C07C 2/78* | (2006.01) |
| *C07C 2/80* | (2006.01) |
| *C07C 2/84* | (2006.01) |
| *C07C 7/09* | (2006.01) |
| *C09C 1/48* | (2006.01) |

(52) U.S. Cl.
CPC ............ *C01B 32/05* (2017.08); *C01B 32/162* (2017.08); *C01B 32/205* (2017.08); *C07C 2/78* (2013.01); *C07C 2/80* (2013.01); *C07C 2/84* (2013.01); *C07C 7/09* (2013.01); *C09C 1/48* (2013.01); *C01B 2203/0277* (2013.01); *C01B 2203/062* (2013.01); *C01B 2203/1047* (2013.01); *C01P 2006/80* (2013.01); *C07C 2521/04* (2013.01); *C07C 2523/745* (2013.01)

(58) Field of Classification Search
CPC ... C07C 2523/745; B01J 21/04; B01J 23/745; C01B 3/26; C01B 32/05; C01B 32/162; C01B 32/205; C01B 2203/0277; C01B 2203/062; C01B 2203/1047; C09C 1/48; C01P 2006/80
See application file for complete search history.

(56) References Cited

OTHER PUBLICATIONS

Zhou et al. ("Fe catalysts for methane decomposition to produce hydrogen and carbon nano materials." Applied catalysis B: environmental 208 (2017): 44-59) (Year: 2017).*

Liu et al. ("Nonoxidative Methane Conversion to Acetylene over Zeolite in a Low Temperature Plasma." Journal of Catalysis 179, 326-334 (1998)) (Year: 1998).*

* cited by examiner

PROCESS FOR PRODUCING HYDROGEN, CARBON, AND ETHYLENE FROM METHANE-CONTAINING FEEDSTOCK

CROSS REFERENCE TO RELATED APPLICATION

This application claims priority to Korean Patent Application No. 10-2021-0146261, filed Oct. 29, 2021, the disclosure of which is hereby incorporated by reference in its entirety.

BACKGROUND OF THE INVENTION

Field of the Invention

The present disclosure relates to a process for producing hydrogen, carbon, and ethylene from a methane-containing feedstock. More particularly, the present disclosure relates to a method for producing hydrogen, carbon, and ethylene from a methane-containing feedstock even without recycling of unreacted methane by providing a single process or system in which a methane-containing feedstock is subjected to two methane conversion steps, including a first conversion step of producing hydrogen and carbonaceous (or carbon-based) materials and a second conversion step of producing acetylene from unreacted methane and hydrogen discharged from the first conversion step while maintaining good methane conversion and suppressing coke formation, followed by separating and recovering ethylene and hydrogen produced through selective hydrogenation of acetylene.

Description of Related Art

Methane is the most abundant compound in natural gas, and accounts for twice the amount of carbon as other known fossil fuel sources. Specifically, it has been reported that natural gas reserves are more extensive than those of coal and oil put together. With the gradual depletion of coal and oil reserves, the utilization of natural gas is having a significant impact on the global energy balance. Hence, the supply of natural gas such as methane is expected to last for more than 20 years longer than petroleum resources, and thus natural gas is emerging as the most realistic alternative raw material to replace petroleum in the era of depletion of petroleum resources and high oil prices. Thorough research on technologies for converting methane into heavier value-added materials, such as olefins (particularly ethylene), aromatics, naphtha, fuel oil, etc., is ongoing.

A direct conversion method and an indirect conversion method are known methods for converting methane into heavier hydrocarbons. The indirect conversion method mainly involves the production of synthesis gas through steam reforming, etc., while the direct conversion method does not involve an intermediate step such as the production of synthesis gas. Currently, most commercialized value-added processes for methane produce hydrocarbon compounds from synthesis gas generated through partial oxidation of methane. For example, in the Fischer-Tropsch process, hydrocarbons and the like are produced from synthesis gas using a metal catalyst (Co, Fe). However, indirect conversion technology requires several steps to be performed, so the reaction efficiency could be low, and it is difficult to attain economic feasibility owing to high processing costs attributable to high-temperature and high-pressure operating conditions.

As an alternative thereto, a method of directly converting methane, without the need to produce synthesis gas, has been proposed. In the conventional art, the production of C2+ hydrocarbons (e.g. C2 hydrocarbons such as ethane, ethylene, and/or acetylene and aromatics such as benzene) through oxidative coupling of methane has been proposed (e.g. Korean Patent Application Publication No. 10-2018-0113448 and the like). Another known direct methane conversion is to produce C2+ hydrocarbons using a non-oxidative route.

However, as for the direct conversion process, undesirable byproducts are formed, for example carbon oxides (CO, $CO_2$, etc.) in the oxidative conversion mode and coke, which leads to deactivation of the catalyst in the non-oxidative conversion mode. Nevertheless, studies for solving problems such as coke formation while maximizing the advantages of the direct conversion method are ongoing.

In addition, hydrogen is inevitably generated during the conversion of methane into value-added C2+ hydrocarbons (i.e. dehydrogenation). Hydrogen has high energy efficiency per unit mass, and generates only water upon combustion, without any other harmful byproducts. Based on these advantageous characteristics, the value of hydrogen as a clean energy source has increased recently. If hydrogen formed as a byproduct of the dehydrogenation during methane pyrolysis is effectively recovered, it would be advantageous in terms of the economic feasibility of the entire process.

In addition, carbonaceous materials (i.e., carbon-based materials) may be a representative example of value-added products that may be prepared from methane. Such a carbon-based material may be used as a fuel or the like, but when used as an electrode material for an energy storage device such as secondary batteries, supercapacitors, etc., the value thereof may be further increased.

Therefore, it would be desirable to achieve commercial-scale production of various value-added materials from methane having relatively low value using a simple process or system.

SUMMARY OF THE INVENTION

An embodiment of the present disclosure purports to provide an efficient method capable of simultaneously producing carbonaceous materials, ethylene, and high-purity hydrogen from a methane-containing feedstock through a single process or system.

Another embodiment of the present disclosure is intended to provide an efficient process capable not only of eliminating difficulty in the separation/recovery of ethylene, hydrogen, etc., the need for recycling of methane, and the like, due to unreacted methane resulting from a methane conversion process, but also of increasing the conversion of methane and suppressing the formation of byproducts such as coke.

An aspect of the present disclosure provides a method for producing carbon (C), ethylene ($C_2H_4$), and hydrogen ($H_2$) from methane, comprising the steps of:

step a) forming a first product comprising unreacted methane, carbon, and hydrogen through methane pyrolysis by transferring a methane-containing feedstock to a first methane conversion step, step b) separating a first gaseous mixture containing hydrogen and methane and solid carbonaceous materials from the first product, step c) forming a second gaseous mixture containing hydrogen and acetylene through a methane coupling reaction by transferring the first gaseous mixture to a second methane conversion step, step d) forming a third gaseous mixture containing hydrogen and ethylene by subjecting acetylene in the second gaseous mixture to selective hydrogenation in the presence of a hydrogenation catalyst, and step e) separating and recovering hydrogen and ethylene, respectively, from the third gaseous mixture.

According to an exemplary embodiment, the hydrogen ($H_2$)/methane ($CH_4$) molar ratio in the first gaseous mixture may be adjusted within the range of 1 to 6, and the hydrogen ($H_2$)/acetylene ($C_2H_2$) molar ratio in the second gaseous mixture may be adjusted within the range of 20 to 150.

According to an exemplary embodiment, the hydrogen ($H_2$)/ethylene ($C_2H_4$) molar ratio in the third gaseous mixture may be adjusted within the range of 20 to 110.

According to an exemplary embodiment, the purity of the hydrogen separated in step e) may be at least 97%.

According to an exemplary embodiment, the hydrogenation catalyst may comprise:

a porous support; and an active metal loaded on the porous support, in which the active metal comprises, (i) a first metal $M_1$ having hydrogenation activity and (ii) a second metal $M_2$ having a function of inducing selective hydrogenation.

According to an exemplary embodiment, the first metal $M_1$ may be at least one selected from the group consisting of Pd, Pt, Rh, Ir, Ni, and Co, and the second metal $M_2$ may be at least one selected from the group consisting of Cu, Ag, Au, Zn, Ga, and Sn, where each amount of the first metal $M_1$ and the second metal $M_2$ in the hydrogenation catalyst is 0.1 to 2 wt % and 0.2 to 40 wt %, and satisfies Equation 2 below:

$$1 \leq \frac{W_{M2}}{W_{M1}} \leq 20 \quad \text{[Equation 2]}$$

wherein $W_{M1}$ is wt % of the first metal in the hydrogenation catalyst and $W_{M2}$ is wt % of the second metal in the hydrogenation catalyst.

BRIEF DESCRIPTION OF THE DRAWINGS

The above and other objects, features, and other advantages of the present invention will be more clearly understood from the following detailed description taken in conjunction with the accompanying drawings, in which.

DESCRIPTION OF THE INVENTION

Figure 1:
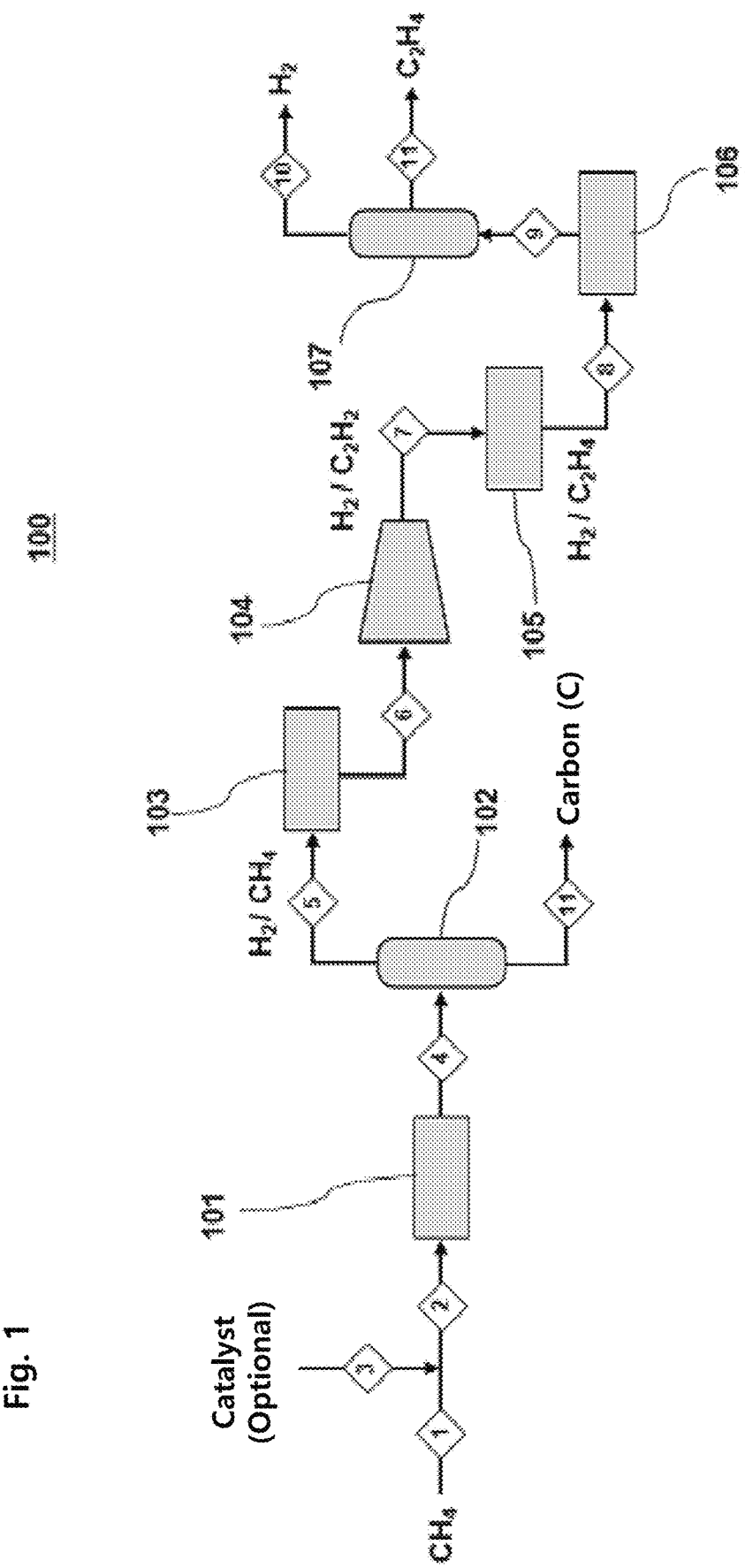
FIG. 1 schematically shows a single process for the production of carbonaceous materials, ethylene, and hydrogen from a methane-containing feedstock according to an exemplary embodiment.

The present invention can be worked in its entirety based on the following description. It should be understood that the following description is given of preferred embodiments of the present invention, and the present invention is not necessarily limited thereto. In addition, the accompanying drawings are provided to aid understanding of the present invention, and the present invention is not limited thereto.

Terms used herein may be defined as follows.

The term "coke" may refer to a hydrocarbon having low hydrogen content, particularly a residual solid carbon byproduct, which may cause deactivation of the catalyst when deposited on the catalyst.

The term "coupling" may narrowly refer to a chemical reaction in which two identical molecules react to form a larger molecule in a narrow sense.

The term "methane coupling" may refer to a reaction that forms not only $C_2$ hydrocarbons (e.g. ethane, ethylene, acetylene, etc.) from methane, but also larger hydrocarbon ($C_{2+}$) dimers (e.g. propane, butane, benzene, naphthalene, etc.), hydrogen ($H_2$), and the like. For example, methane may be activated to form free methyl radicals and to be converted into ethane, which is then converted into ethylene through a dehydrogenation reaction, and additionally ethylene may be converted into acetylene through a dehydrogenation reaction, and furthermore, heavier hydrocarbons may be formed through the generation of hydrocarbon radicals.

The term "pyrolysis" may refer to a reaction in which hydrocarbons are decomposed upon exposure to heat or the like, even without the addition of oxygen or oxygen-containing reactants, and in the present disclosure, may be construed to include a reaction that converts a compound into one or more other materials by applying heat thereto.

The term "catalytic decomposition of methane (CDM)" may refer to a chemical reaction that forms solid carbon (or carbonaceous materials) and a hydrogen molecule in a gas phase from a methane molecule.

The term "plasma" may refer to an ionized gas, particularly one in a state in which cations, electrons, and neutral gases (radicals) are mixed due to separation of electrons from molecules or atoms.

The term "plasma pyrolysis of methane" may refer to a reaction in which methane is pyrolyzed in a gas phase by plasma, thus directly forming hydrogen and forms solid carbon (or carbonaceous materials), during which carbon dioxide and the like are not generated as byproducts.

The term "plasma coupling of methane" may refer to a reaction in which methane is converted into C2+ hydrocarbons, hydrogen, etc. using plasma.

The term "heterogeneous catalyst" may refer to a catalyst that exists in a phase different from that of a reactant during a catalytic reaction, for example, a catalyst that is not dissolved in a reaction medium. For a heterogeneous catalyst, in order for the reaction to occur, at least one reactant has to be diffused and adsorbed to the surface of the heterogeneous catalyst, and after the reaction, the product needs to be desorbed from the surface of the heterogeneous catalyst.

The term "support" may refer to a material (typically a solid material) having a high specific surface area, and onto which a catalytically active component is attached or deposited.

The term "hydrogenation" may refer to a reaction in which hydrogen content in a compound is increased by chemically adding hydrogen to at least a portion of the compound by bringing the compound into contact with a catalyst in the presence of hydrogen.

The term "impregnation" may refer to a method of preparing a catalyst by impregnating a support with a solution in which a catalyst precursor is dissolved and then performing drying and/or firing (or reduction treatment) as necessary.

The term "conversion" may refer to the number of moles of the feedstock that are converted into a compound other than the feedstock per unit mole thereof.

The term "selectivity" may refer to the number of moles of a target product per unit mole of the converted feedstock.

An embodiment of the present disclosure pertains to a process for producing carbonaceous materials, ethylene, and hydrogen with high quality from a methane-containing feedstock through a single process or system including two methane conversion steps and a selective hydrogenation step, which is illustrated in FIG. 1.

With reference to this drawing, the methane-containing feedstock may be in a gas form, and may be introduced into a methane conversion process 100 via a line 1. According to an exemplary embodiment, the methane-containing feedstock may be at least one selected from pure methane, liquefied natural gas (LNG), natural gas, a mixed gas containing methane as a main component (e.g. at least about 50 vol %, particularly at least about 80 vol %, more particularly at least about 90 vol %), and the like. In this regard, natural gas mainly contains methane, and may further contain hydrocarbon gas components other than methane (e.g. at least one selected from the group consisting of ethane, propane, and heavier hydrocarbons) and/or a diluent gas (e.g. at least one selected from the group consisting of nitrogen, oxygen, carbon dioxide, helium, and hydrogen sulfide). Here, the concentration of the diluent gas in the feedstock may be, for example, about 15 vol % or less, particularly about 12 vol % or less, and more particularly about 10 vol % or less.

Catalytic Decomposition of Methane (First Methane Conversion Step)

With reference to FIG. 1, a methane pyrolysis unit 101 is not limited to a specific type, so long as it is able to convert methane into carbon and hydrogen, but may be exemplified by a catalytic decomposition unit or a plasma-assisted pyrolysis unit. Here, the catalyst may be combined with the methane-containing feedstock via a line 3 and introduced into the methane pyrolysis unit 101 via a line 2.

In conventional techniques, a steam reforming method is mainly used to produce hydrogen from methane. In this method, carbon dioxide, which corresponds to a greenhouse gas, is generated as well as hydrogen. Also, methane, which is a stable nonpolar molecule present as an inert gas, has C—H binding energy of about 435 kJ/mol, and thus has high thermodynamic stability and is not easy to decompose, making it difficult to convert methane into heavier hydrocarbons through a coupling reaction.

According to the illustrated embodiment, in the pyrolysis unit 101, hydrogen in a gas phase and carbon in a solid phase are produced through the reaction represented in Scheme 1 below.

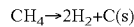

[Scheme 1]

In the above Scheme, the theoretical energy required to produce 1 mole of hydrogen is about 37.8 kJ/mol, which is lower than about 63.3 kJ/mol required for the steam reforming of methane, and carbon dioxide is not generated.

According to an exemplary embodiment, the methane pyrolysis may be a catalytic decomposition reaction. Since a strong C—H bond of a methane molecule has to be cleaved, a high-temperature condition has to be maintained, and a catalyst may be used to lower the high heat of reaction.

According to an exemplary embodiment, a transition-metal-based catalyst, particularly an iron (Fe)-based catalyst, may be used during the catalytic decomposition reaction. According to a specific embodiment, the iron-based catalyst may be at least one selected from among, for example, iron ore, an iron-supported catalyst, and the like. For example, the iron ore may be at least one selected from among types having crystalline structures of hematite ($\alpha$-$Fe_2O_3$), maghemite ($\gamma$-$Fe_2O_3$), and magnetite ($Fe_3O_4$) in oxide forms. According to a further specific embodiment, the particle size of the iron (Fe)-based catalyst may be in the range of, for example, about 0.1 to 150 μm, particularly about 20 to 120 μm, and more particularly about 30 to 110 μm, as measured using a particle size analyzer. Also, according to a specific embodiment, the iron (Fe)-based catalyst may be nanoparticles, and the particle size thereof may be in the range of, for example, about 5 to 100 nm, particularly about 10 to 70 nm, and more particularly about 20 to 50 nm, as measured using a nanoparticle size analyzer.

Furthermore, for the iron-supported catalyst, the support may be at least one porous inorganic oxide selected from among, for example, alumina ($Al_2O_3$), silica ($SiO_2$), magnesia (MgO), titania ($TiO_2$), zirconia ($ZrO_2$), and the like. Alternatively, a support made of an organic material, particularly a carbon (carbide) material, may be used, as in a Fe/C catalyst. By way of example, the porous support may have a specific surface area (BET) of about 100 to 200 $m^2/g$ (particularly about 130 to 180 $m^2/g$, more particularly about 150 to 170 $m^2/g$), and a pore volume of about 0.4 to 1 $cm^3/g$ (particularly about 0.5 to 0.9 $cm^3/g$, more particularly about 0.6 to 0.8 $cm^3/g$). Moreover, the amount of iron (which may be in the form of elemental iron and/or iron oxide) in the iron-supported catalyst may be in the range of, for example, about 5 to 40 wt %, particularly about 7 to 20 wt %, more particularly about 9 to about 15 wt %.

According to an exemplary embodiment, the catalytic pyrolysis unit or reactor may be selected from among a fluidized-bed reactor, a rotary-type, rotary-kiln-type, or screw-kiln-type reactor, a moving-bed reactor, and the like, and more particularly, a fluidized-bed reactor or a screw kiln-type reactor may be used.

According to an exemplary embodiment, the catalytic decomposition temperature of methane may be adjusted within the range of, for example, about 600 to 950° C., particularly about 700 to 900° C., and more particularly about 750 to 850° C. Also, the residence time in the reactor may be adjusted within the range of, for example, about 5 to 150 hours, particularly about 10 to 120 hours, and more particularly about 15 to 100 hours.

Here, in the catalytic decomposition reaction of methane, unreacted methane may exist in addition to hydrogen and carbon, and the reaction conditions may be controlled, so the ratio between hydrogen and methane in the product (i.e. the first product 4) may be adjusted so as to form a composition suitable for the subsequent second methane conversion step (i.e. a methane coupling reaction). Specifically, when the internal temperature of the methane catalytic decomposition reactor rises, the conversion of methane no longer increases because thermodynamic equilibrium between methane, carbon, and hydrogen is established during the catalytic pyrolysis, and consequently, the first product 4 contains unreacted methane.

In consideration thereof, in the present embodiment, it is possible to provide a gaseous composition suitable for the second methane conversion step by adjusting the relative ratio between unreacted methane and hydrogen generated during the pyrolysis. For example, when the methane conversion is maintained relatively low and the gas hourly space velocity (or residence time) is increased, the amount of hydrogen that is produced per unit weight of catalytically active metal (for which the unit is $gH_2/gFe$ when the active metal is Fe) may be increased, whereas when the methane conversion is maintained relatively high and the gas hourly space velocity (or residence time) is decreased, the amount of hydrogen that is produced per unit weight of catalytically active metal may be decreased.

According to an exemplary embodiment, the conversion of methane in the methane decomposition reaction may be adjusted within the range of, for example, about 60 to 90%, particularly about 62 to 80%, more particularly about 65 to 75%, and still more particularly about 70%. Here, operation at a higher reaction temperature enables the methane conversion to be increased to 90% or more, but the amount of hydrogen that is produced per unit mass of catalytically active metal may be decreased because of heat loss due to high-temperature operation and increased deactivation of the catalyst, making it difficult to achieve a desired hydrogen/methane ratio. Hence, the methane conversion may be controlled, depending on the desired amount of carbon to be produced, a hydrogen/methane ratio suitable for the subsequent second methane conversion step, and the like.

According to an alternative embodiment, in the first methane conversion step, methane pyrolysis may be performed using a plasma-assisted methane pyrolysis reactor, particularly a thermal plasma reactor, more particularly a high-temperature plasma reactor, instead of the methane catalytic pyrolysis unit. As such, the plasma may be formed in a manner of generating a strong electric field in the target gas so that accelerated electrons generate a sufficient number of charged domains through successive collisions and a field having electrical conductivity is formed to maintain a plasma state. Since the plasma state may accelerate a thermodynamically dominant chemical reaction, it may be utilized to produce hydrogen and carbon (i.e. solid carbonaceous materials) without the use of a catalyst.

According to an exemplary embodiment, the plasma pyrolysis may involve heating a plasma gas using electric energy. Here, the plasma gas may be heated using an electric arc. Also, the plasma gas may be applied in an oxygen-free atmosphere, the oxygen in the oxygen-free atmosphere being adjusted to less than about 3 vol %, particularly less than about 1 vol %.

According to an exemplary embodiment, the plasma gas may be at least one selected from among hydrogen, helium, argon, neon, nitrogen, and the like, and more particularly nitrogen or hydrogen may be used.

According to an exemplary embodiment, high-energy electron excitation is induced in a plasma-assisted pyrolysis reactor to form radicals, and carbon and hydrogen may be produced according to Scheme 2 below.

[Scheme 2]

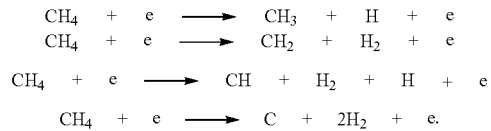

According to an exemplary embodiment, the plasma reactor may be operable in both high-temperature and low-temperature plasma modes, and may be selected from among, for example, an arc torch reactor, an inductively coupled plasma reactor, a microwave plasma reactor, and the like, and may also operate under pressure conditions of atmospheric pressure or more. By way of example, the internal temperature of the plasma reactor may be adjusted within the range of, for example, about 1000 to 2000° C., particularly about 1200 to 1800° C., and more particularly about 1300 to 1400° C., and the pressure may be adjusted to approximate atmospheric pressure. Also, as an additional reaction condition, the plasma power may be adjusted within the range of about 1 to 100 kW, particularly about 10 to 70 kW, and more particularly about 30 to 50 kW per unit of plasma that is supplied.

Separation and Recovery of Carbon from Methane Catalytic Decomposition Product

According to an exemplary embodiment, solid carbonaceous materials are formed along with hydrogen through the first methane conversion step. Here, the amount of carbon in a solid phase in the first product 4 may be in the range of, for example, about 80 to 95 wt %, particularly about 85 to 93 wt %, and more particularly about 87 to 90 wt %, but the above ranges are set forth merely for illustrative purposes.

The first product 4 is separated into solid-phase carbon (carbonaceous materials; 11), as a bottom stream, and a gas mixture (a first gaseous mixture; 5) containing hydrogen and unreacted methane, as an overhead stream, through the gas-solid separation process. In this regard, separating and recovering carbon from the first product may be performed before the methane coupling reaction in the second methane conversion step. To this end, a gas-solid separator known in the art, for example, a cyclone, a hydrocyclone, a gravity settling device, a spray scrubber, a venturi scrubber, a bag filter, a pocket filter, an electric precipitator, etc., may be used.

Here, the hydrogen ($H_2$)/methane ($CH_4$) molar ratio may be adjusted within the range of, for example, about 1 to 6, particularly about 2 to 5.5, and more particularly about 3 to 5, and may be approximately 4.7 in a specific embodiment, resulting from controlling the methane pyrolysis conditions so as to form a composition suitable for the subsequent second methane conversion step.

According to an exemplary embodiment, it is preferable to selectively synthesize hydrogen and carbon from methane in the first methane conversion step, so it may be advantageous to adjust the amount of C2+ hydrocarbons in the first gaseous mixture 5 to be less than a predetermined level, for example, less than about 1 mol %, particularly less than about 0.5 mol %, and more particularly less than about 0.1 mol %. In particular, the amount of aromatics (particularly, C6+ aromatic hydrocarbons) in the C2+ hydrocarbons may be, for example, less than about 1 mol %, particularly less than about 0.5 mol %, and more particularly less than about 0.1 mol %.

In addition, the carbon 11 in a solid phase that is separated may be recovered. Here, the recovered carbonaceous materials may be of a different type depending on the methane decomposition method or conditions, and may be at least one selected from among, for example, graphite, carbon black, carbon nanotubes, amorphous carbon, and the like. For example, graphite, amorphous carbon, etc. may be produced in the catalytic decomposition reaction of methane, while carbon black may be mainly produced in the plasma-assisted methane pyrolysis reaction. In a specific embodiment, the carbon-based material may be graphite, so additional treatment may be performed to increase the purity of carbon or the crystallinity of carbon.

Methane Coupling Reaction (Second Methane Conversion Step)

Referring again to FIG. 1, the first gaseous mixture 5 is transferred to a second methane conversion unit 103 to undergo a methane coupling reaction, particularly a direct non-oxidative methane coupling reaction. In this regard, the methane coupling reactor is not limited to a particular type, but may be a radial tube reactor suitable for high-temperature operation. Also, the material for the pyrolysis reactor may be at least one selected from among, for example, alumina, SiC, FeCrAl alloy, Inconel (NiCr), and the like.

According to the present embodiment, in the second methane conversion step, C2+ hydrocarbons and hydrogen (as a byproduct) may be produced from methane through methane coupling by thermal conversion or methane coupling using plasma. This methane coupling reaction is carried out under controlled reaction conditions (temperature, pressure, residence time, etc.) for the purpose of increasing the methane conversion and minimizing coke formation. In particular, when the methane coupling reaction is performed in the presence of hydrogen, methane is mainly converted into acetylene rather than ethylene. In other words, by controlling the conditions of the methane coupling reaction, the conversion of methane and the selectivity for acetylene is increased, while coke formation is suppressed.

In the thermal conversion route, since the radical reaction is performed after methane is activated into methyl radicals, the reaction temperature and pressure conditions are precisely controlled in order to increase the methane conversion and suppress coke formation.

For example, the temperature of the thermal conversion may be adjusted within the range of, for example, about 1100 to 1500° C., particularly about 1150 to 1475° C., more particularly about 1200 to 1450° C., and still more particularly about 1300 to 1400° C. Also, the total pressure of the thermal conversion may be adjusted within the range of, for example, about 0.1 to 1 bar, particularly about 0.2 to 0.8 bar, more particularly about 0.3 to 0.7 bar, and still more particularly about 0.4 to 0.6 bar.

In a specific embodiment, the partial pressure of hydrogen and the partial pressure of methane in the methane coupling reactor may satisfy the requirement represented by Equation 1 below.

$$\frac{P_{H_2}}{P_{CH_4}} > 0 \quad \text{[Equation 1]}$$

wherein, $P_{H_2}$ is the partial pressure of hydrogen in the mixed gas introduced into the reactor and $P_{CH_4}$ is the partial pressure of methane in the mixed gas introduced into the reactor.

According to an exemplary embodiment, $$\frac{P_{H_2}}{P_{CH_4}}$$

may be adjusted within the range of, for example, about 2 to 22, particularly about 4 to 20, and more particularly about 4.5 to 18.

Optionally, the methane coupling reaction using the thermal conversion may be carried out in the presence of a catalyst (e.g. a supported catalyst), and a metal having a methane activation function may be at least one selected from among iron (Fe), chromium (Cr), vanadium (V), molybdenum (Mo), tungsten (W), and the like. Also, the support may be a porous support made of an inorganic oxide material, for example, at least one selected from among alumina, silica, titania, zirconia, magnesia, ceria, and the like. The amount of the active metal in the catalyst may be adjusted within the range of, for example, about 0.1 to 10 wt %, particularly about 0.3 to 8 wt %, and more particularly about 0.5 to 5 wt %. The catalyst composition described above is set forth merely for illustrative purposes, and the present disclosure is not necessarily limited thereto.

In addition, the gas hourly space velocity (GHSV) in the methane coupling reaction using thermal conversion may be set within the range of, for example, about 500 to 2000 hr$^{-1}$, particularly about 550 to 1000 hr$^{-1}$, and more particularly about 570 to 900 hr$^{-1}$.

As such, when the non-oxidative methane coupling reaction is carried out under high-temperature and low-pressure conditions by providing unreacted methane and concomitantly produced hydrogen in the first methane conversion step as reactants, a second gaseous mixture 6 containing C2 hydrocarbons (especially acetylene) and hydrogen is mainly produced.

According to an exemplary embodiment, the residence time of the gas mixture containing methane and hydrogen (i.e. the first gaseous mixture) supplied to the methane coupling reaction unit 103 may be adjusted within the range of, for example, about 1 to 10 seconds, particularly about 2 to 8 seconds, and more particularly about 3 to 7 seconds.

According to an alternative embodiment, the second methane conversion step may be performed using a plasma reactor. As the plasma reactor, any type known in the art may be used, and the plasma reactor may be selected from among a low-temperature inductively coupled plasma reactor, a microwave plasma reactor, an arc torch reactor, and the like.

In an exemplary embodiment, the internal temperature of the plasma reactor may be set within the range of, for example, at least about 1000° C., particularly about 1200 to 2000° C., and more particularly about 1300 to 1500° C. Also, the plasma reaction may be carried out under relatively low pressure conditions, for example, less than about 0.2 bar, particularly less than about 0.1 bar, and more particularly less than about 0.075 bar. Since the inside of the plasma reactor is maintained at a high temperature, when the product remains in the reactor for an excessively long time, selectivity for acetylene may be lowered, so it may be advantageous to set an appropriate reaction time. For example, the reaction time or residence time may be set within the range of, for example, about 0.1 to 2 seconds, particularly about 0.5 to 1.5 seconds, and more particularly about 0.75 to 1.25 seconds.

In addition, when using the plasma reactor, the hydrogen/methane molar ratio in the first gaseous mixture 5 that is supplied may be adjusted to a level similar to that in the above thermal conversion method, and may be set within the range of, for example, about 1 to 3, particularly about 1.5 to 2.5, and more particularly about 1.75 to 2.25, but the above ranges are set forth merely for illustrative purposes, and may be changed in consideration of the type of plasma reactor, reaction conditions, and the like.

According to an exemplary embodiment, the methane conversion in the second methane conversion step described above may be, for example, at least about 35%, at least about 40%, at least about 45%, at least about 50%, at least about 60%, or at least about 70%. In a specific embodiment, the methane conversion may be at least about 80%, particularly at least about 90%, more particularly at least about 98%, and still more particularly at least about 99%, and may be close to about 100%. However, if there are any problems associated with other factors in the reaction system, such as temperature compensation, etc., the conversion may be adjusted to about 60% or less. Here, the above ranges are set forth merely for illustrative purposes.

The selectivity for acetylene may also be, for example, at least about 60%, particularly at least about 70%, and more particularly at least about 80%. However, since the selectivity for ethylene among C2 hydrocarbons may increase with an increase in the reaction pressure, precise control of the reaction conditions may be required in order to increase the selectivity for acetylene.

As such, most of the methane is converted to result in high acetylene selectivity, so the amount of methane in the second gaseous mixture 6 may be, for example, less than about 7.5 mol %, particularly less than about 3 mol %. More particularly, the second gaseous mixture may be substantially free of methane.

In addition, the amount of C2 hydrocarbons other than acetylene, such as ethane and/or ethylene, among C2 hydrocarbons resulting from the methane coupling reaction, may be, for example, less than about 40 mol %, particularly less than about 30 mol %, and more particularly less than about 20 mol %. According to a specific embodiment, the concentration of ethylene in the second gaseous mixture 6 may be, for example, less than about 1 mol %, particularly less than about 0.7 mol %, and more particularly less than about 0.2 mol %.

In addition, the second gaseous mixture 6 may further contain, as impurities, C3 to C5 hydrocarbons that may be generated during the methane coupling reaction, but the amount of these hydrocarbons may be typically less than about 0.1 mol %, particularly less than about 0.05 mol %, and more particularly less than about 0.01 mol %. Furthermore, since the methane coupling reaction does not use oxygen, the second gaseous mixture may be substantially free of carbon monoxide, carbon dioxide, and the like.

According to an exemplary embodiment, the hydrogen ($H_2$)/acetylene ($C_2H_2$) molar ratio in the second gaseous mixture 6 may be adjusted within the range of, for example, about 20 to 150, particularly about 30 to 120, and more particularly about 40 to 100.

Referring again to FIG. 1, the second gaseous mixture 6 is transferred to a hydrogenation unit 105. Here, in order to increase the conversion in the selective acetylene hydrogenation, a vacuum pump (or a depressurization pump 104) may be optionally disposed upstream of the hydrogenation unit 105, and thus the pressure of the second gaseous mixture may be decreased to, for example, about 0.1 to 2 bar, particularly about 0.3 to 1 bar, and more particularly about 0.5 to 0.7 bar. Consequently, the depressurized second gaseous mixture 7 may contain acetylene as a main component, among hydrocarbons. However, the vacuum pump may be omitted depending on the reaction conditions and the like.

Selective Hydrogenation

According to the illustrated embodiment, in the hydrogenation unit 105, acetylene in the gaseous mixture 7 may be converted into ethylene through selective hydrogenation using a catalyst. Here, the hydrogen contained in the second gaseous mixture may be used as it is without the need to separately or externally supply hydrogen necessary for the acetylene hydrogenation. Although hydrogen supplementation from the outside to reach a hydrogen partial pressure suitable for effective hydrogenation of acetylene is not strictly excluded, the amount of hydrogen that is added may be greatly decreased in such cases.

The hydrogenation may be carried out in the presence of a catalyst. Here, it is necessary to use a catalyst having activity capable of increasing the conversion of acetylene and the selectivity for ethylene. To this end, the hydrogenation is carried out in the presence of a heterogeneous catalyst in which at least two metals, particularly a first metal $M_1$ having hydrogenation activity and a second metal $M_2$ having a function of inducing selective hydrogenation, are loaded on a porous support. Since this metal function may be quantified with H adatom adsorption energy through DFT calculations, the first metal $M_1$ may exhibit hydrogen adsorption energy of, for example, about $-4$ to $-2$ eV and the second metal $M_2$ may exhibit hydrogen adsorption energy of, for example, about $-1$ to $0$ eV.

By way of example, the first metal $M_1$ may be at least one selected from the group consisting of Pd, Pt, Rh, Ir, Ni, and Co, and particularly may be Pd. Also, the second metal $M_2$ may be at least one selected from the group consisting of Cu, Ag, Au, Zn, Ga, and Sn, and particularly may be Cu. According to a specific embodiment, the combination of metals loaded on the support may be a combination of Pd and Cu, and the reason for use thereof may be explained by the alloying effect. The hydrogenation catalyst used in the present embodiment is a catalyst comprising two species of active metal components, and the first metal (particularly Pd) and the second metal (particularly Cu) may be in a state showing crystallinity, and may also be in an alloy form or in a supported form while coming into close contact with each other. In addition, the first metal $M_1$ may exist in the form of a single atom, and the second metal $M_2$ may exist in the form of nanoparticles.

In an exemplary embodiment, the size of the active metal (or each of the first and second metals) in the hydrogenation catalyst may be, for example, about 100 nm or less, particularly about 10 to 70 nm, and more particularly about 20 to 50 nm.

According to an embodiment, the amount of the first metal $M_1$ in the hydrogenation catalyst may be, for example, about 0.1 to 2 wt %, particularly about 0.2 to 1 wt %, more particularly about 0.3 to 0.8 wt %, and still more particularly about 0.4 to 0.5 wt %. Since the amount of the first metal affects selective hydrogenation activity and selectivity, it may be advantageous to set the same within the above range. Also, the amount of the second metal $M_2$ may be, for example, about 0.2 to 40 wt %, particularly about 0.5 to 20 wt %, more particularly about 1 to 15 wt %, and still more particularly about 2 to 5 wt %. If the amount of the second metal is excessively high or low, activity and selectivity may be decreased. Hence, the amount of the second metal may be set within the above range.

Meanwhile, in an exemplary embodiment, the first metal $M_1$ and the second metal $M_2$ may be combined at a predetermined ratio taking into consideration the properties of each metal. In this regard, the hydrogenation catalyst may satisfy Equation 2 below.

$$1 \le \frac{W_{M2}}{W_{M1}} \le 20 \quad \text{[Equation 2]}$$

wherein, $W_{M1}$ is wt % of the first metal in the hydrogenation catalyst and $W_{M2}$ is wt % of the second metal in the hydrogenation catalyst.

According to an exemplary embodiment, $$\frac{W_{M2}}{W_{M1}}$$

may be adjusted within the range of, for example, about 2 to 10, particularly about 3 to 8, and more particularly about 4 to 7. If the amount of the first metal $M_1$ relative to the second metal $M_2$ falls outside a predetermined range, activity may be deteriorated, or a phenomenon by which selectivity decreases during the hydrogenation may occur. Hence, it may be advantageous to appropriately adjust the amount thereof within the above range.

Also, the support for loading the two metals (the first and second metals) may be at least one selected from the group consisting of alumina, silica, carbon, zirconia, titania, ceria, and silicon carbide. Particularly, alumina, and more particularly gamma-alumina, may be used.

According to an exemplary embodiment, the support may be a porous support, and the porosity thereof may be controlled such that the reactant or product does not have an excessively long residence time when diffusing in the support.

In this regard, the support for the hydrogenation may exhibit properties exemplified below:
 Specific surface area (BET): at least about 300 m$^2$/g, particularly about 400 to 700 m$^2$/g, and more particularly about 500 to 600 m$^2$/g;
 Pore volume: at least about 0.5 cm$^3$/g, particularly about 0.75 to 2 cm$^3$/g, and more particularly about 1 to 1.5 cm$^3$/g; and
 Average pore size: about 50 to 200 Å, particularly about 70 to 180 Å, and more particularly about 100 to 150 Å.

According to an exemplary embodiment, the support may be prepared in various shapes known in the art, as well as in a powder form. Examples thereof may include a spherical shape (including a hollow shape), a cylindrical shape (including a hollow shape), a granular shape, a tablet shape, a ring shape, a saddle shape, a star shape, a honeycomb shape, a pellet shape, a trilobe shape, a quadrilobe shape, and the like. As such, for illustrative purposes, in order to prepare a support having a specific shape, any molding techniques known in the art, e.g., extrusion, spray drying, pelletizing, oil dropping, etc. may be performed. Also, the average size of the support having a shape exemplified above or in a molded form may be in the range of, for example, about 1 to 5 mm, particularly about 1.5 to 3 mm, and more particularly about 2 to 2.75 mm, which are set forth merely for illustrative purposes.

According to an exemplary embodiment, the hydrogenation catalyst may be prepared through a supporting method known in the art, examples of which may include an impregnation method, a deposition method, an ion-exchange method, deposition-precipitation, etc. Particularly, an impregnation method, and more particularly, incipient (wetness) impregnation or modified incipient (wetness) impregnation, may be applied.

In a specific embodiment, the catalyst may be prepared through an impregnation method. To this end, the metal may be used in the form of a precursor, particularly a metal compound, more particularly a metal salt, a complex, etc., and may be selected from among types that are soluble in the medium used to prepare the impregnation solution (particularly, an aqueous medium). For example, when the first metal among the active metals is palladium, a precursor thereof may be an organic acid salt or an inorganic acid salt, a complex, a hydroxide, a halide, or a combination thereof. For example, a palladium precursor may be at least one selected from among palladium acetate, palladium chloride, palladium nitrate, palladium ammonium nitrate, palladium sulfate, palladium carbonate, palladium hydroxide, palladium halide, hydrates thereof, and the like, which are set forth merely for illustrative purposes. More typically, palladium ammonium nitrate may be used as the precursor. On the other hand, when the second metal is copper, the precursor thereof may be at least one selected from among, for example, copper hydroxide phosphate, copper nitrate, copper sulfate, copper acetate, copper formate, copper (II) chloride, copper iodide, and the like, and more typically, copper nitrate may be used.

According to an exemplary embodiment, the impregnation solution may be prepared by sequentially or simultaneously adding the first metal precursor and the second metal precursor to the medium. Here, the total concentration of the active metal precursors (the first metal precursor and the second metal precursor) in the impregnation solution may be adjusted within the range of, for example, about 0.01 to 2 µM, particularly about 0.1 to 1 µM, and more particularly about 0.25 to 0.75 µM, depending on the amounts of the first and second metals that are supported in the final catalyst and the ratio between the first metal and the second metal.

In addition, the pH of the solution containing the first metal precursor and the second metal precursor may be adjusted within the range of, for example, about 1 to 3, particularly about 1.2 to 2, and more particularly about 1.3 to 1.5, in order to effectively disperse the metal precursor in the support. For this, any acid components known in the art may be added to the impregnation solution. Such an acid component may be at least one selected from among nitric acid, sulfuric acid, hydrochloric acid, oxalic acid, and the like.

The impregnation process is not limited to any particular process, so long as the metal precursor solution (i.e. the composite precursor solution of the first and second metals) is able to sufficiently contact the pores in the support. For example, the metal precursor solution may be sprayed for contact or impregnation, thus forming a precursor solid. Alternatively, the support may be immersed in the metal precursor solution, for example, at about 15 to 80° C. (particularly at about 20 to 50° C., more particularly at room temperature) for about 0.5 to 3 hours (particularly about 1 to 2 hours). However, these conditions are set forth merely for illustrative purposes.

After impregnation of the support with the active metals as described above, a drying step may be performed, for example, in an oxygen-containing atmosphere (particularly, ambient air). Here, the drying temperature may be set within the range of, for example, about 60 to 150° C., particularly about 70 to 100° C., but is not limited thereto. Also, the drying time may be set within the range of, for example, about 3 to 24 hours, particularly about 6 to 12 hours. Through the drying step, the metal precursor may be more closely attached to the support. Ultimately, there may be provided a structure in which the support is covered with the active metal precursors, for instance, a core-shell structure.

After the solid in which the first metal precursor and the second metal precursor are attached or deposited onto the support is obtained as described above, the metal component may be converted into a reduced or elemental form through reduction treatment. Here, although calcination or heat treatment before reduction treatment is not excluded, the reduction of the precursor solid without calcination treatment may be adopted.

The reduction treatment may be performed using hydrogen alone or hydrogen diluted with an inert gas (e.g. $N_2$, He, Ar, etc.), and may be carried out in the temperature range of, for example, about 200 to 400° C., particularly about 220 to 380° C., and more particularly about 250 to 350° C. Here, the heating rate may be set within the range of, for example, about 3 to 10° C./min, particularly about 4 to 8° C./min, and more particularly about 5 to 7° C./min. Also, the reduction time is not particularly limited, and may be adjusted within the range of, for example, about 0.5 to 24 hours, particularly about 1 to 12 hours. By way of example, when the reducing gas is diluted with the inert gas, the concentration of the reducing gas may be in the range of, for example, about 5 to 20 vol %. In addition, the pressure during the reduction treatment may be in the range of, for example, atmospheric pressure to 10 bar (typically atmospheric pressure).

According to an embodiment, the second gaseous mixture is hydrogenated in the hydrogenation unit 105 in the presence of the catalyst described above. Here, the hydrogenation temperature may be set within the range from room temperature to 250° C., particularly about 40 to 200° C., and more particularly about 50 to 150° C. Also, the hydrogenation pressure may be set within the range of, for example, about 0.2 to 1 bar, particularly about 0.3 to 0.8 bar, and more particularly about 0.4 to 0.7 bar.

According to an exemplary embodiment, the selective hydrogenation may be performed in a batch or continuous mode, but a continuous mode is preferable due to economic feasibility of operation and the like. Here, the reactor is not particularly limited, but, for example, a gaseous fixed-bed reactor, a fluidized-bed reactor, etc. may be used. In particular, a fixed-bed reactor may be advantageously used. Moreover, the gas hourly space velocity (GHSV) is determined, depending on both the ethylene productivity and the conversion through catalytic contact. If the gas hourly space velocity is excessively low, productivity may be deteriorated, whereas if the gas hourly space velocity is excessively high, contact with the catalyst may become insufficient. In consideration thereof, the gas hourly space velocity may be adjusted within the range of, for example, about 1 to 15 $L/g_{cat}·hr^{-1}$, particularly about 2 to 10 $L/g_{cat}·hr^{-1}$, and more particularly about 3 to 5 $L/g_{cat}·hr^{-1}$.

According to an exemplary embodiment, the conversion of acetylene in the second gaseous mixture 7 as the reactant may be in the range of, for example, at least about 40%, at least about 45%, at least about 50%, at least about 55%, at least about 60%, at least about 65%, at least about 70%, at least about 75%, at least about 80%, at least about 85%, at least about 90%, at least about 95%, at least about 97.5%, or about 99 to 99.9%. Also, the selectivity for ethylene may be in the range of, for example, at least about 70%, at least about 75%, at least about 80%, at least about 85%, at least about 90%, at least about 95%, at least about 97.5%, or about 99% to 99.9%. However, the above numerical ranges are set forth merely for illustrative purposes.

As described above, the third gaseous mixture 8, containing hydrogen and ethylene due to the selective hydrogenation of acetylene, is discharged from the hydrogenation unit 105. In this regard, the hydrogen ($H_2$)/ethylene ($C_2H_4$) molar ratio in the third gaseous mixture 8 may be adjusted within the range of, for example, about 20 to 110, particularly about 50 to 105, and more particularly about 70 to 100.

Thereafter, the third gaseous mixture 8 may be subjected to a pressurization process to facilitate separation of hydrogen and ethylene. In the illustrated embodiment, the third gaseous mixture may be pressurized while passing through a process gas compressor 106, and may be pressurized to, for example, at least about 10 bar, particularly about 15 to 50 bar, and more particularly about 20 to 30 bar.

Recovery of Hydrogen and Ethylene

With reference to FIG. 1, the pressurized third gaseous mixture 9 may be separated and recovered into hydrogen 10 and ethylene 11 through a separator. Such a separator may be, for example, a separation column, particularly a C2 splitter, or the like. According to the illustrated embodiment, the separator may be a separation column 107, and easy separation may be possible using a difference in boiling point between hydrogen and ethylene (ethylene: −103.7° C., hydrogen: −252.9° C.). In particular, most of the methane supplied to the entire reaction process is converted through the preceding two-step methane conversion reaction, whereby a separation process between methane (boiling point: −161.6° C.) and hydrogen or between methane and ethylene may be easily configured. Further, since the third gaseous mixture 9 contains almost no methane, not only ethylene but also high-purity hydrogen may be obtained therefrom without recycling. In addition, a hydrogen/methane mixed gas having a controlled composition is formed in the first methane conversion step and then supplied to the methane coupling reaction in the second methane conversion step under a controlled reaction conditions, whereby coke formation may be suppressed and the methane conversion may be maximized, so at least three types of value-added compounds may be simply obtained through a single process in which a plurality of reaction units is arranged in time series.

A better understanding of the present invention may be obtained through the following examples, which are merely set forth to illustrate the present invention and are not to be construed as limiting the scope of the present invention.

EXAMPLE 1

Methane Catalytic Pyrolysis (First Methane Conversion Step)

Iron Ore, the main component of which is iron oxide having a hematite crystal structure, was used as a catalyst, and was used as received, without separate treatment. As such, the particle size of the iron ore was about 45 to 106 μm, and Fe content was about 65 to 70 wt % (based on XRF analysis).

As a catalyst, 1.5 g of iron ore was placed in the center in the longitudinal direction of a reactor (a stainless steel material, outer diameter: 25.4 mm, inner diameter: 22.9 mm). Here, the reactor was oxidized and carbonized before reaction, and non-reactivity thereof was confirmed. Methane and nitrogen were supplied at a volume ratio of 90:10, and the fluid was supplied to the top of the reactor (feed rate: 10 mL/min). Also, the reaction temperature was fixed to 850° C. and the reaction pressure was fixed to 1 bar.

EXAMPLE 2

A methane catalytic pyrolysis reaction was performed in the same manner as in Example 1, with the exception that the reaction temperature was changed to 800° C.

EXAMPLE 3

A methane catalytic pyrolysis was performed in the same manner as in Example 1, with the exception that the reaction temperature was changed to 750° C.

EXAMPLE 4

Methane Coupling Reaction (Second Methane Conversion Step)

A methane coupling reaction was performed using an alumina reactor ($Al_2O_3$, outer diameter: 13 mm, inner diameter: 9 mm). Specifically, methane at a volume flow rate of 2 mL/min, hydrogen at 36 mL/min, and nitrogen at 10 mL/min were supplied through an external tube. The reaction temperature was maintained at 1325° C. and the reaction pressure was maintained at 0.5 bar.

EXAMPLE 5

A methane coupling reaction was performed under the same conditions as in Example 4, with the exception that methane at a volume flow rate of 4 mL/min, hydrogen at 32 mL/min, and nitrogen at 10 mL/min were supplied through an external tube.

EXAMPLE 6

A methane coupling reaction was performed under the same conditions as in Example 4, with the exception that methane at a volume flow rate of 6 mL/min, hydrogen at 28 mL/min, and nitrogen at 10 mL/min were supplied through an external tube.

EXAMPLE 7

A methane coupling reaction was performed under the same conditions as in Example 5, except that the reaction pressure was maintained at 0.75 bar.

EXAMPLE 8

A methane coupling reaction was performed under the same conditions as in Example 5, with the exception that the reaction pressure was maintained at 1 bar.

EXAMPLE 9

A methane coupling reaction was performed under the same conditions as in Example 4, with the exception that methane at a volume flow rate of 3 mL/min, hydrogen at 54 mL/min, and nitrogen at 10 mL/min were supplied through an external tube.

EXAMPLE 10

A methane coupling reaction was performed under the same conditions as in Example 4, with the exception that methane at a volume flow rate of 4 mL/min, hydrogen at 72 mL/min, and nitrogen at 10 mL/min were supplied through an external tube.

TEST EXAMPLES

Methane Catalytic Pyrolysis Reaction

The gaseous hydrocarbons obtained after the methane catalytic pyrolysis according to each of Examples 1 to 3 were analyzed using a 7890A GC from Agilent. The gaseous products were analyzed using a Restek Molesieve Micro-packed column-connected Thermal Conductivity Detector (TCD) and an HP-PLOT Q bond-connected Flame Ionization Detector (FID). In addition, $H_2$, $N_2$, $CH_4$, $O_2$, and CO were separated on Molesieve Micropacked columns and detected by TCD, and the conversion was calculated using the integrated area of $CH_4$ relative to the integrated area of $N_2$ according to an internal standard. In addition, C1-C6 light hydrocarbons were separated on an HP-PLOT Q bond column and detected by FID, and C7 or larger compounds were not analyzed. The carbon balance was determined to be 99% or more through the above assay.

Methane Coupling Reaction

The gaseous product obtained after the methane coupling reaction according to each of Examples 4 to 10 was analyzed using a Restek Molesieve Micropacked column-connected Thermal Conductivity Detector (TCD) and an HP-PLOT Q bond-connected Flame Ionization Detector (FID). The gaseous hydrocarbons obtained after the reaction were analyzed using a 7890A GC from Agilent. In addition, $H_2$, $N_2$, $CH_4$, $O_2$, and CO were separated on Molesieve Micropacked columns and detected by TCD, and the conversion was calculated using the integrated area of $CH_4$ relative to the integrated area of $N_2$ according to an internal standard. In addition, C1-C6 light hydrocarbons were separated on an HP-PLOT Q bond column and detected by FID, and C7 or larger compounds were not analyzed. The carbon balance was determined to be 99% or more through the above assay.

Test Results

Figure 2:
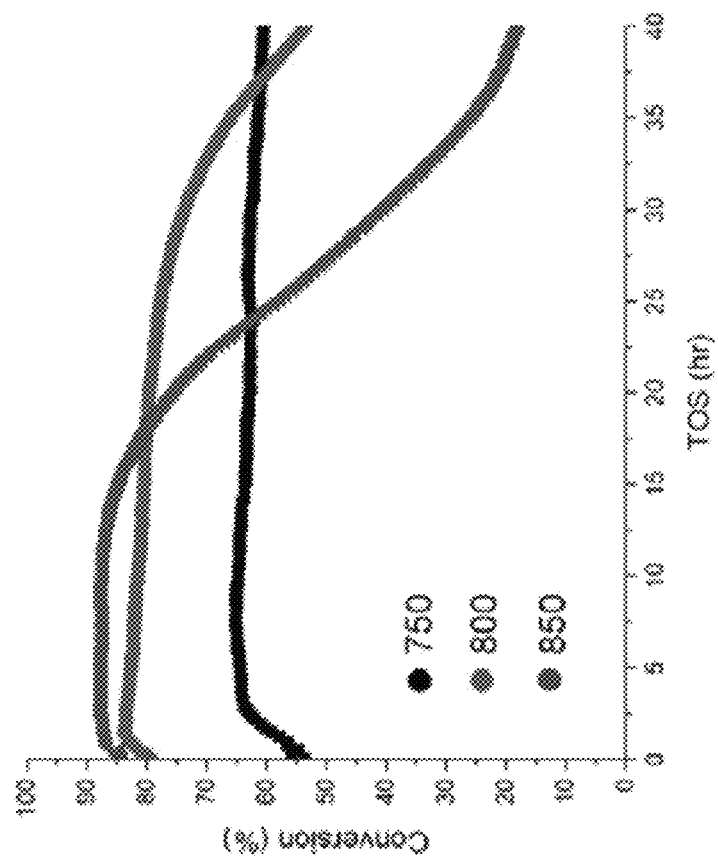
FIG. 2 is a graph showing the methane conversion depending on TOS (time on stream) at different temperatures (750° C., 800° C., and 850° C.) in a catalytic pyrolysis reaction of methane.

The results of measurement of the methane conversion depending on changes in the reaction temperature in the methane catalytic pyrolysis according to Examples 1 to 3 are shown in FIG. 2.

With reference to the above drawing, the methane conversion was about 70% when the catalytic pyrolysis temperature was 750° C. (Example 3), was about 80% when the pyrolysis temperature was 800° C. (Example 2), and was increased to 90% when the pyrolysis temperature was 850° C. (Example 1), but the methane conversion was rapidly decreased after 15 hours due to deactivation of the catalyst. Also, in Example 1, when the reaction was carried out under conditions of a reaction temperature of 850° C. and a reaction time of 15 hours, the average methane conversion was about 87.0% and the amount of hydrogen that was produced per unit mass of catalytically active metal was 1.2 $gH_2/gFe$. In Example 2, when the reaction was carried out under conditions of a reaction temperature of 800° C. and a reaction time of 25 hours, the average methane conversion was about 80.9% and the amount of hydrogen that was produced per unit mass of catalytically active metal was 2.0 $gH_2/gFe$. Also, in Example 3, when the reaction was carried out under conditions of a reaction temperature of 750° C. and a reaction time of 45 hours, the average methane conversion was about 62.6% and the amount of hydrogen that was produced per unit mass of catalytically active metal was 2.93 $gH_2/gFe$. As such, when the reaction temperature was lower, the methane conversion was decreased but the amount of hydrogen that was produced per unit mass of catalytically active metal was increased.

Figure 3:
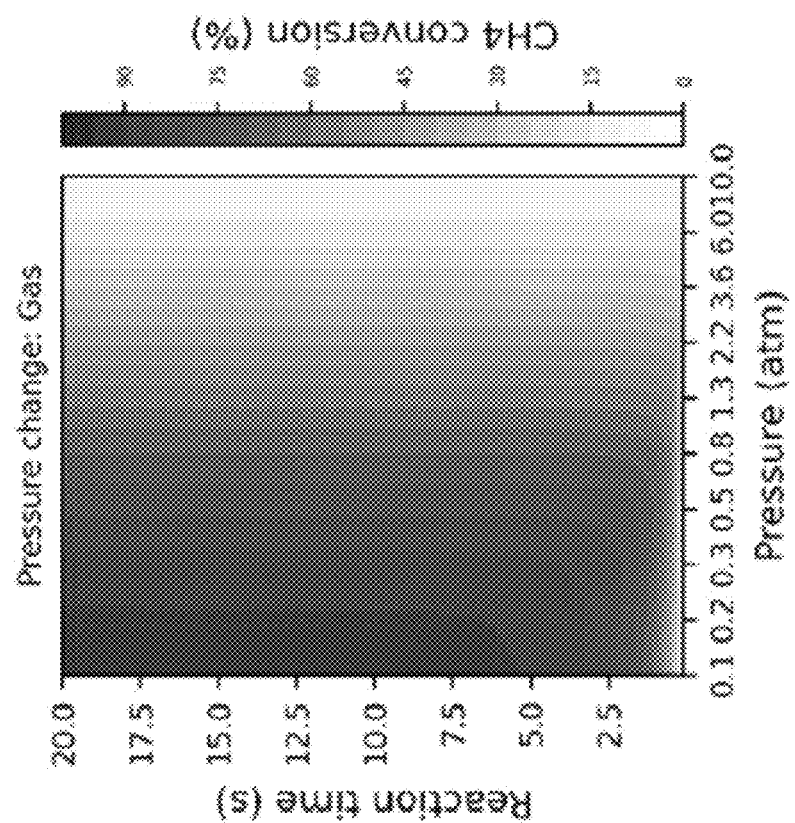
FIG. 3 shows simulation results in a methane coupling reaction under conditions of supply of methane (initial partial pressure: 0.18 atm) and hydrogen (initial partial pressure: 0.82 atm) and a temperature of 1325° C.
Figure 4:
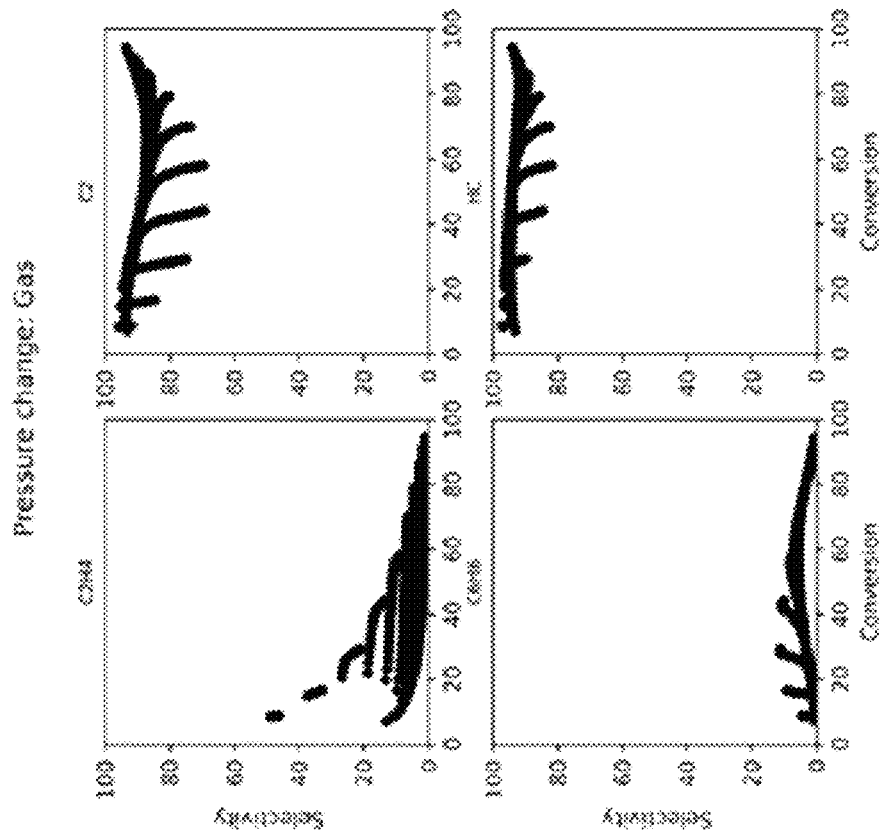
FIG. 4 shows simulation results plotting selectivity for each of $C_2H_4$, $C_2$, $C_6H_6$, and HC (in which $C_2$ means the sum of $C_2H_6$, $C_2H_4$, and $C_2H_2$), versus the methane conversion in the methane coupling reaction under conditions of supply of methane (initial partial pressure: 0.18 atm) and hydrogen (initial partial pressure: 0.82 atm) and a temperature of 1325° C.
Figure 5:
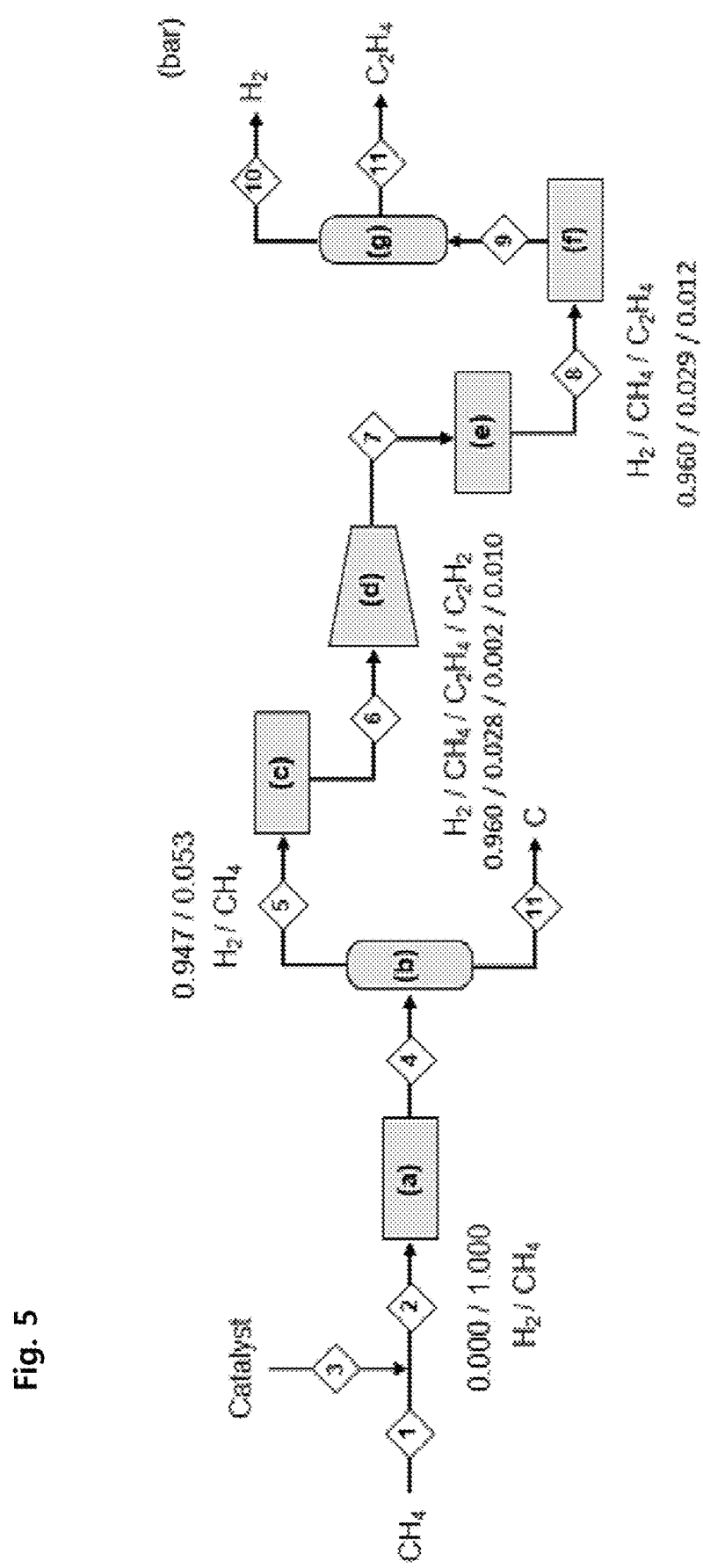
FIG. 5 shows the processing conditions for each unit and the composition for each flow (or stream) in a single process for producing carbonaceous materials, ethylene, and hydrogen from a methane-containing feedstock, in which the conversion of a methane catalytic pyrolysis reaction is about 90%, the conversion of a methane coupling reaction is about 45%, and the conversion of an acetylene selective hydrogenation reaction is about 99.9%.

In the methane coupling reaction according to Examples 4 to 6, simulation results under conditions of supply of methane (initial partial pressure: 0.18 atm) and hydrogen (initial partial pressure: 0.82 atm) and a temperature of 1300° C., and simulation results plotting the selectivity for each of $C_2H_4$, $O_2$, $C_6H_6$, and HC versus the methane conversion are shown in FIGS. 3 and 4, respectively.

With reference to the above drawings, when the reaction temperature was 1300° C. and the partial pressure ratio of introduced methane and hydrogen was 0.18:0.82, the methane conversion was increased with a decrease in the pressure. Here, the partial pressures of methane and hydrogen correspond to the same gas composition as in the case in which the methane conversion was 70% in the preceding methane catalytic pyrolysis. When methane was converted into hydrocarbons under the aforementioned high-temperature and low-pressure conditions, C2 hydrocarbons were mainly produced, which is supported by the simulation results shown in FIG. 4. C2 hydrocarbons are the sum of ethane, ethylene, and acetylene, and are mainly analyzed as the sum of ethylene and acetylene. The main component of C2 hydrocarbons is acetylene.

In Examples 4 to 6, the methane coupling reaction was carried out using, as respective reactants, the products of the methane catalytic pyrolysis corresponding to Examples 1 to 3 (methane conversion of Example 1: 90%; methane conversion of Example 2: 80%; methane conversion of Example 3: 70%), and the resulting methane conversion and product distribution are shown in Table 1 below.

TABLE 1

| Example | Introduced flow ($CH_4/H_2$) mL/min | Temp. (° C.) | Pressure (Bar) | Methane conversion rate | Methane coupling product flow ($CH_4$, $H_2$, $C_2H_4$, $C_2H_2$) (mL/min) |
| --- | --- | --- | --- | --- | --- |
| 4 | 2/36 | 1325 | 0.5 | 45.16 | 1.10/37.28/0.07/0.38 |
| 5 | 4/32 | 1325 | 0.5 | 54.31 | 1.83/35.08/0.18/0.90 |
| 6 | 6/28 | 1325 | 0.5 | 54.09 | 2.75/32.58/0.28/1.34 |

As is apparent from Table 1, C2 hydrocarbons (acetylene and ethylene) can be continuously produced in association with the products of methane catalytic pyrolysis. The methane conversion and product yield in the methane coupling reaction are affected by the hydrogen/methane ratio, temperature, pressure, and gas hourly space velocity, and particularly, in Examples 4 to 6, since the hydrogen/methane ratio was high, C2 hydrocarbons, especially acetylene, were mainly produced.

In addition, the net methane conversion obtained when the methane catalytic pyrolysis and the methane coupling reaction were performed sequentially are shown in Table 2 below.

TABLE 2

| Example | Net methane conversion (%) | $H_2$ purity (%) |
| --- | --- | --- |
| 4 | 94.52 | 97.14 |
| 5 | 90.86 | 95.05 |
| 6 | 86.23 | 92.21 |

As is apparent from Table 2, when the methane catalytic pyrolysis and the methane coupling reaction were performed sequentially, the net methane conversion was 94.52% (Example 4), 90.86% (Example 5), and 86.23% (Example 6). Moreover, the purity of hydrogen in the gas excluding C2 hydrocarbons (ethylene and acetylene) was 97.14% (Example 4), 95.05% (Example 5), and 92.21% (Example 6). When the methane catalytic pyrolysis and the methane coupling reaction are sequentially performed and the temperature of the methane coupling reaction is elevated to 1350° C. or higher, it can be expected that the methane conversion is maintained at 90% or more, and also that, when the conversion is 90% or more, the purity of hydrogen is 99.48% or more.

In the methane coupling reaction, the methane conversion and product yield are determined by the hydrogen/methane ratio, temperature, pressure, and gas hourly space velocity, and thus the effect of pressure was analyzed based on Examples 5, 7, and 8, and the results thereof are shown in Table 3 below.

TABLE 3

| Example | Introduced flow ($CH_4/H_2$) mL/min | Temp. (° C.) | Pressure (Bar) | Methane conversion rate | Methane coupling product flow ($CH_4$, $H_2$, $C_2H_4$, $C_2H_2$) (mL/min) |
| --- | --- | --- | --- | --- | --- |
| 5 | 4/32 | 1325 | 0.5 | 54.31 | 1.83/35.08/0.18/0.90 |
| 7 | 4/32 | 1325 | 0.75 | 51.45 | 1.94/34.80/0.28/0.74 |
| 8 | 4/32 | 1325 | 1 | 47.01 | 2.12/34.48/0.33/0.60 |

Table 3 shows the results of setting the pressure of the methane coupling reaction to 0.5 bar, 0.75 bar, and 1 bar when the methane conversion was 80% in the methane catalytic pyrolysis.

When the pressure of the methane coupling reaction was 0.5 bar (Example 5), 0.75 bar (Example 7), and 1 bar (Example 8), the methane conversion was 54.31%, 51.45% and 47.01%, respectively. As mentioned in the simulation results according to FIG. 4, it can be seen that the methane conversion in the methane coupling reaction decreased with an increase in the reaction pressure.

In addition, the net methane conversion obtained when the methane catalytic pyrolysis and the methane coupling reaction were performed sequentially are shown in Table 4 below.

TABLE 4

| Example | Net methane conversion (%) | $H_2$ purity (%) |
| --- | --- | --- |
| 5 | 90.86 | 95.05 |
| 7 | 90.29 | 94.71 |
| 8 | 89.40 | 94.21 |

As is apparent from Table 4, when the methane catalytic pyrolysis and the methane coupling reaction were performed sequentially, the net methane conversion was 90.29% (Example 7) and 89.40% (Example 8). Also, the purity of hydrogen in the gas excluding C2 hydrocarbons (ethylene and acetylene) was 94.71% (Example 7) and 94.21% (Example 8).

In the methane coupling reaction, the methane conversion and product yield are determined by the hydrogen/methane ratio, temperature, pressure, and gas hourly space velocity, and thus the effect of gas hourly space velocity was analyzed based on Examples 4, 9, and 10, and the results thereof are shown in Table 5 below.

TABLE 5

| Example | Introduced flow ($CH_4/H_2$) mL/min | Temp. (° C.) | Pressure (Bar) | Methane conversion rate | Methane coupling product flow ($CH_4$, $H_2$, $C_2H_4$, $C_2H_2$) (mL/min) |
|---|---|---|---|---|---|
| 4 | 2/36 | 1325 | 0.5 | 45.16 | 1.10/37.28/ 0.07/0.38 |
| 9 | 3/54 | 1325 | 0.5 | 41.84 | 1.74/55.79/ 0.09/0.53 |
| 10 | 4/72 | 1325 | 0.5 | 35.15 | 2.59/73.93/ 0.18/0.52 |

Table 5 shows the results of setting the volume flow rates of the reactants to 38 mL/min, 57 mL/min, and 76 mL/min in the methane coupling reaction when the methane conversion was 80% in the methane catalytic pyrolysis.

When the volume flow rates of the reactants were 38 mL/min (Example 4), 57 mL/min (Example 9), and 76 mL/min (Example 10), the methane conversion was 45.16%, 41.84%, and 35.15%, respectively. As mentioned in the simulation results according to FIG. 4, it can be seen that the methane conversion in the methane coupling reaction decreased with an increase in the residence time of the reactants.

In addition, the net methane conversion rates obtained when the methane catalytic pyrolysis reaction and the methane coupling reaction were performed sequentially are shown in Table 6 below.

TABLE 6

| Example | Net methane conversion (%) | $H_2$ purity (%) |
|---|---|---|
| 4 | 94.52 | 97.14 |
| 9 | 94.18 | 96.97 |
| 10 | 93.52 | 96.61 |

As is apparent from Table 6, when the methane catalytic pyrolysis and the methane coupling reaction were performed sequentially, the net methane conversion was 94.18% (Example 9) and 93.52% (Example 10). Also, the purity of hydrogen in the gas excluding C2 hydrocarbons (ethylene and acetylene) was 96.97% (Example 9) and 96.61% (Example 10).

Taking into consideration the results according to Examples 4 to 10, by adjusting the temperature conditions of the methane catalytic pyrolysis and the hydrogen/methane ratio, the reaction pressure, the gas hourly space velocity, and the reaction temperature of the methane coupling reaction, hydrogen and acetylene can be produced from methane. In particular, it is noteworthy that hydrogen having high purity of 97% or more can be produced.

Moreover, by maintaining the reaction temperature at 850° C. under atmospheric pressure during the methane catalytic pyrolysis and adjusting the temperature of the methane coupling reaction within the range of 1325 to 1375° C., when the methane conversion of the methane coupling reaction is maintained at 90%, hydrogen having purity of 99.48% can be produced, and when the methane conversion is maintained at 95%, hydrogen having purity of 99.74% can be produced. Also, when the methane conversion is maintained at 99%, hydrogen having purity of 99.95% can be produced without recycling of unreacted methane.

By maintaining the reaction temperature at 800° C. under atmospheric pressure during the methane catalytic pyrolysis and adjusting the temperature of the methane coupling reaction within the range of 1325 to 1375° C., when the methane conversion of the methane coupling reaction is maintained at 90%, hydrogen having purity of 98.93% can be produced, and when the methane conversion is maintained at 95%, hydrogen having purity of 99.47% can be produced. Also, when the methane conversion rate is maintained at 99%, hydrogen having purity of 99.89% can be produced without recycling of unreacted methane.

Furthermore, by maintaining the reaction temperature at 750° C. under atmospheric pressure during the methane catalytic pyrolysis and adjusting the temperature of the methane coupling reaction within the range of 1325 to 1375° C., when the methane conversion of the methane coupling reaction is maintained at 90%, hydrogen having purity of 98.34% can be produced, and when the methane conversion is maintained at 95%, hydrogen having purity of 99.17% can be produced. Also, when the methane conversion is maintained at 99%, hydrogen having purity of 99.84% can be produced without recycling of unreacted methane.

As is apparent from the above description, a process according to an embodiment of the present disclosure is capable of producing carbonaceous materials, high-purity hydrogen, and ethylene from a methane-containing feedstock through a single process or system in which two methane conversion steps (units), a selective hydrogenation step (unit), and an ethylene/hydrogen separation step (unit) are arranged in time series. In particular, the ratio between unreacted methane and hydrogen in the product of the first methane conversion step is adjusted to form a composition suitable for a methane coupling reaction occurring in the second methane conversion step, whereby selective conversion into acetylene is enhanced, and moreover, coke formation can be effectively suppressed. Furthermore, methane content in the product resulting from selective hydrogenation of acetylene is minimized, thus alleviating difficulty in separation of methane from hydrogen (or ethylene), and, ethylene and hydrogen can be easily separated, advantageously producing both hydrogen and ethylene with high quality. In addition, this process is particularly advantageous for commercialization as it can achieve a high methane conversion even without recycling of reactants.

Simple modifications or variations of the present invention can be easily devised by those of ordinary skill in the art, and all such modifications or variations can be considered to include the scope of the present invention.

The invention claimed is:

1. A method for producing carbon (C), ethylene ($C_2H_4$), and hydrogen ($H_2$) from methane, comprising the steps of:
   step a) forming a first product comprising unreacted methane, carbon, and hydrogen through methane pyrolysis by transferring a methane-containing feedstock to a first methane conversion step;
   step b) separating a first gaseous mixture containing hydrogen and methane and solid carbonaceous materials from the first product, wherein a hydrogen ($H_2$)/methane ($CH_4$) molar ratio in the first gaseous mixture is adjusted within a range of 1 to 6;

step c) forming a second gaseous mixture containing hydrogen and acetylene through a methane coupling reaction by transferring the first gaseous mixture to a second methane conversion step,
  wherein the second methane conversion step is performed through a direct non-oxidative methane coupling reaction by thermal conversion,
  wherein in the second methane conversion step, a methane conversion is at least 35% and selectivity for acetylene is at least 60%, and
  wherein a hydrogen ($H_2$)/acetylene ($C_2H_2$) molar ratio in the second gaseous mixture is adjusted within a range of 20 to 150;
step d) forming a third gaseous mixture containing hydrogen and ethylene by subjecting acetylene in the second gaseous mixture to selective hydrogenation in the presence of a hydrogenation catalyst; and
step e) separating and recovering hydrogen and ethylene, respectively, from the third gaseous mixture.

2. The method of claim 1, wherein a hydrogen ($H_2$)/ethylene ($C_2H_4$) molar ratio in the third gaseous mixture is adjusted within a range of 20 to 110.

3. The method of claim 1, wherein a purity of the hydrogen separated in step e) is at least 97%.

4. The method of claim 1, wherein the hydrogenation catalyst comprises:
  a porous support; and
  an active metal loaded on the porous support,
  wherein the active metal comprises (i) a first metal ($M_1$) having hydrogenation activity and (ii) a second metal ($M_2$) having a function of inducing selective hydrogenation.

5. The method of claim 4, wherein the first metal ($M_1$) is at least one selected from the group consisting of Pd, Pt, Rh, Ir, Ni, and Co, and the second metal ($M_2$) is at least one selected from the group consisting of Cu, Ag, Au, Zn, Ga, and Sn,
  where each amount of the first metal ($M_1$) and the second metal ($M_2$) in the hydrogenation catalyst are 0.1 to 2 wt % and 0.2 to 40 wt %, and satisfies Equation 2 below:

$$1 \leq \frac{W_{M2}}{W_{M1}} \leq 20 \qquad \text{[Equation 2]}$$

wherein $W_{M1}$ is wt % of the first metal in the hydrogenation catalyst and $W_{M2}$ is wt % of the second metal in the hydrogenation catalyst.

6. The method of claim 1, wherein the first methane conversion step is performed through methane catalytic pyrolysis or plasma pyrolysis.

7. The method of claim 6, wherein a catalyst used for the methane catalytic pyrolysis is iron ore or an iron-supported catalyst,
  wherein the iron ore is at least one selected from among types having crystal structures of hematite ($\alpha$-$Fe_2O_3$), maghemite ($\gamma$-$Fe_2O_3$), and magnetite ($Fe_3O_4$), and
  a support in the iron-supported catalyst is at least one porous inorganic oxide selected from the group consisting of alumina ($Al_2O_3$), silica ($SiO_2$), magnesia (MgO), titanic ($TiO_2$), and zirconia ($ZrO_2$), or a carbon material.

8. The method of claim 6, wherein the methane catalytic pyrolysis is performed such that the methane conversion is 30 to 95% under conditions of a temperature of 600 to 950° C. and a residence time of 5 to 150 hours.

9. The method of claim 6, wherein an amount of carbon in the first product obtained in step a) is 80 to 95 wt %, and the carbonaceous materials separated in step b) is at least one selected from the group consisting of graphite, carbon black, carbon nanotubes, and amorphous carbon.

10. The method of claim 1, wherein the direct non-oxidative methane coupling reaction by thermal conversion is performed under conditions of a temperature of 1100 to 1500° C., a total pressure of 0.1 to 1 bar, and a gas hourly space velocity (GHSV) of 500 to 2000 $hr^{-1}$.

11. The method of claim 10, wherein a partial pressure of hydrogen and a partial pressure of methane during the direct non-oxidative methane coupling reaction by thermal conversion satisfy a requirement represented by Equation 1 below:

[Equation 1]

$$\frac{P_{H_2}}{P_{CH_4}} > 0 \qquad \text{[Equation 1]}$$

wherein $P_{H2}$ is a partial pressure of hydrogen in a mixed gas introduced into a reactor and $P_{CH4}$ is a partial pressure of methane in the mixed gas introduced into the reactor.

12. The method of claim 1, wherein the selective hydrogenation reaction is performed under conditions of a temperature ranging from room temperature to 250° C. and a pressure of 0.2 to 1 bar.

13. The method of claim 12, wherein the selective hydrogenation reaction is performed such that an acetylene conversion is at least 40% and selectivity for ethylene is at least 70%.

14. The method of claim 1, wherein step e) is performed using a separation column based on boiling points.

* * * * *

UNITED STATES PATENT AND TRADEMARK OFFICE
CERTIFICATE OF CORRECTION

PATENT NO. : 11,981,632 B2
APPLICATION NO. : 17/976045
DATED : May 14, 2024
INVENTOR(S) : Yun et al.

Page 1 of 1

It is certified that error appears in the above-identified patent and that said Letters Patent is hereby corrected as shown below:

In the Claims

Column 24, Line 10, Claim 7, delete "titanic" and insert -- titania --

Column 24, Lines 30-35, Claim 11, delete
[Equation 1]

" $$\frac{P_{H_2}}{P_{CH_4}} > 0$$ [Equation 1] " and insert

-- [Equation 1]
$$\frac{P_{H_2}}{P_{CH_4}} > 0$$
--

Signed and Sealed this
First Day of October, 2024

Katherine Kelly Vidal
*Director of the United States Patent and Trademark Office*